(12) United States Patent
Cully et al.

(10) Patent No.: US 12,364,798 B2
(45) Date of Patent: Jul. 22, 2025

(54) ANASTOMOTIC DEVICES AND METHODS

(71) Applicant: W. L. Gore & Associates, Inc., Newark, DE (US)

(72) Inventors: Edward H. Cully, Newark, DE (US); Jeffrey B. Duncan, Flagstaff, AZ (US); Karan B. Sangha, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 188 days.

(21) Appl. No.: 18/243,455

(22) Filed: Sep. 7, 2023

(65) Prior Publication Data

US 2023/0414854 A1     Dec. 28, 2023

Related U.S. Application Data

(63) Continuation of application No. 16/291,575, filed on Mar. 4, 2019, now Pat. No. 11,833,288, which is a
(Continued)

(51) Int. Cl.
*A61M 1/36* (2006.01)
*A61B 17/08* (2006.01)
(Continued)

(52) U.S. Cl.
CPC ........... *A61M 1/3655* (2013.01); *A61B 17/11* (2013.01); *A61F 2/064* (2013.01); *A61F 2/07* (2013.01); *A61B 17/08* (2013.01); *A61B 2017/1135* (2013.01); *A61B 2017/1139* (2013.01); *A61F 2002/075* (2013.01); *A61F 2002/8486* (2013.01); *A61F 2/89* (2013.01);
(Continued)

(58) Field of Classification Search
CPC ...... A61M 1/3655; A61B 17/11; A61F 2/064; A61F 2/07; A61F 2002/8486; A61F 2230/0067
See application file for complete search history.

(56) References Cited

U.S. PATENT DOCUMENTS 4,712,551 A    12/1987   Rayhanabad
5,755,778 A    5/1998    Kleshinski
(Continued)

FOREIGN PATENT DOCUMENTS

EP    0964658 A2    12/1999
WO   84/03036 A1    8/1984
(Continued)

OTHER PUBLICATIONS

European Search Report from EP17176551.4, dated Aug. 23, 2017, 10 pages.
(Continued)

*Primary Examiner* — Ashley L Fishback

(57) ABSTRACT

Exemplary embodiments comprise AV fistulas and other anastomotic devices for creating new or reinforcing existing side-branch vessels, and/or bridging neighboring vessels together. An exemplary embodiment may comprise a sidewall port, such as a flanged sidewall port, and/or flow frame design, such as a partially bare, flexible stent or a whisk, for purposes of creating a transmural flow. Another exemplary embodiment may comprise a compliant vessel support to aid in the transition from device to vessel and/or vessel to device, and to promote vessel dilation.

20 Claims, 14 Drawing Sheets

Related U.S. Application Data continuation of application No. 15/267,312, filed on Sep. 16, 2016, now Pat. No. 10,245,371, which is a continuation of application No. 13/229,540, filed on Sep. 9, 2011, now Pat. No. 9,463,269.

(60) Provisional application No. 61/381,655, filed on Sep. 10, 2010.

(51) Int. Cl.
| | | |
|---|---|---|
| *A61B 17/11* | (2006.01) | |
| *A61F 2/06* | (2013.01) | |
| *A61F 2/07* | (2013.01) | |
| *A61F 2/848* | (2013.01) | |
| *A61F 2/89* | (2013.01) | |

(52) U.S. Cl.
CPC ............... *A61F 2230/0067* (2013.01); *A61F 2230/0069* (2013.01)

(56) References Cited

U.S. PATENT DOCUMENTS

| | | |
|---|---|---|
| 5,817,113 A | 10/1998 | Gifford et al. |
| 7,115,136 B2 | 10/2006 | Park et al. |
| 7,780,686 B2 | 8/2010 | Park et al. |
| 8,262,719 B2 | 9/2012 | Erickson et al. |
| 9,463,269 B2 | 10/2016 | Cully et al. |
| 9,554,801 B2 | 1/2017 | Shields et al. |
| 9,782,533 B2 | 10/2017 | Brenneman et al. |
| 10,245,371 B2 | 4/2019 | Cully et al. |
| 10,420,873 B2 | 9/2019 | Shields et al. |
| 10,434,293 B2 | 10/2019 | Park et al. |
| 10,499,920 B2 | 12/2019 | Hall et al. |
| 2001/0053929 A1 | 12/2001 | Vonesh et al. |
| 2002/0165603 A1 | 11/2002 | Thornton et al. |
| 2003/0032967 A1 | 2/2003 | Park et al. |
| 2003/0144671 A1 | 7/2003 | Brooks et al. |
| 2004/0087984 A1 | 5/2004 | Kupiecki et al. |
| 2004/0199177 A1 | 10/2004 | Kim |
| 2006/0225747 A1 | 10/2006 | Maginot |
| 2006/0271166 A1 | 11/2006 | Thill et al. |
| 2007/0233220 A1 | 10/2007 | Greenan |
| 2008/0109069 A1 | 5/2008 | Coleman et al. |
| 2010/0022940 A1 | 1/2010 | Thompson |
| 2010/0130995 A1 | 5/2010 | Yevzlin et al. |
| 2011/0282439 A1 | 11/2011 | Thill et al. |
| 2013/0226067 A1 | 8/2013 | Ward et al. |
| 2019/0231510 A1 | 8/2019 | Rafiee et al. |
| 2019/0298909 A1 | 10/2019 | Cully et al. |

FOREIGN PATENT DOCUMENTS

| | | |
|---|---|---|
| WO | 2003/103513 A1 | 12/2003 |
| WO | 2007/014283 A2 | 2/2007 |
| WO | 2008/112415 A2 | 9/2008 |
| WO | 2009/018583 A1 | 2/2009 |
| WO | 2014/130850 A1 | 8/2014 |
| WO | 2018/236835 A1 | 12/2018 |

OTHER PUBLICATIONS

International Preliminary Report on Patentability received for PCT Patent Application No. PCT/US2011/051133, mailed on Mar. 21, 2013, 16 pages.

International Search Report and Written Opinion from PCT/US2011/051133, dated Feb. 20, 2012, 24 pages.

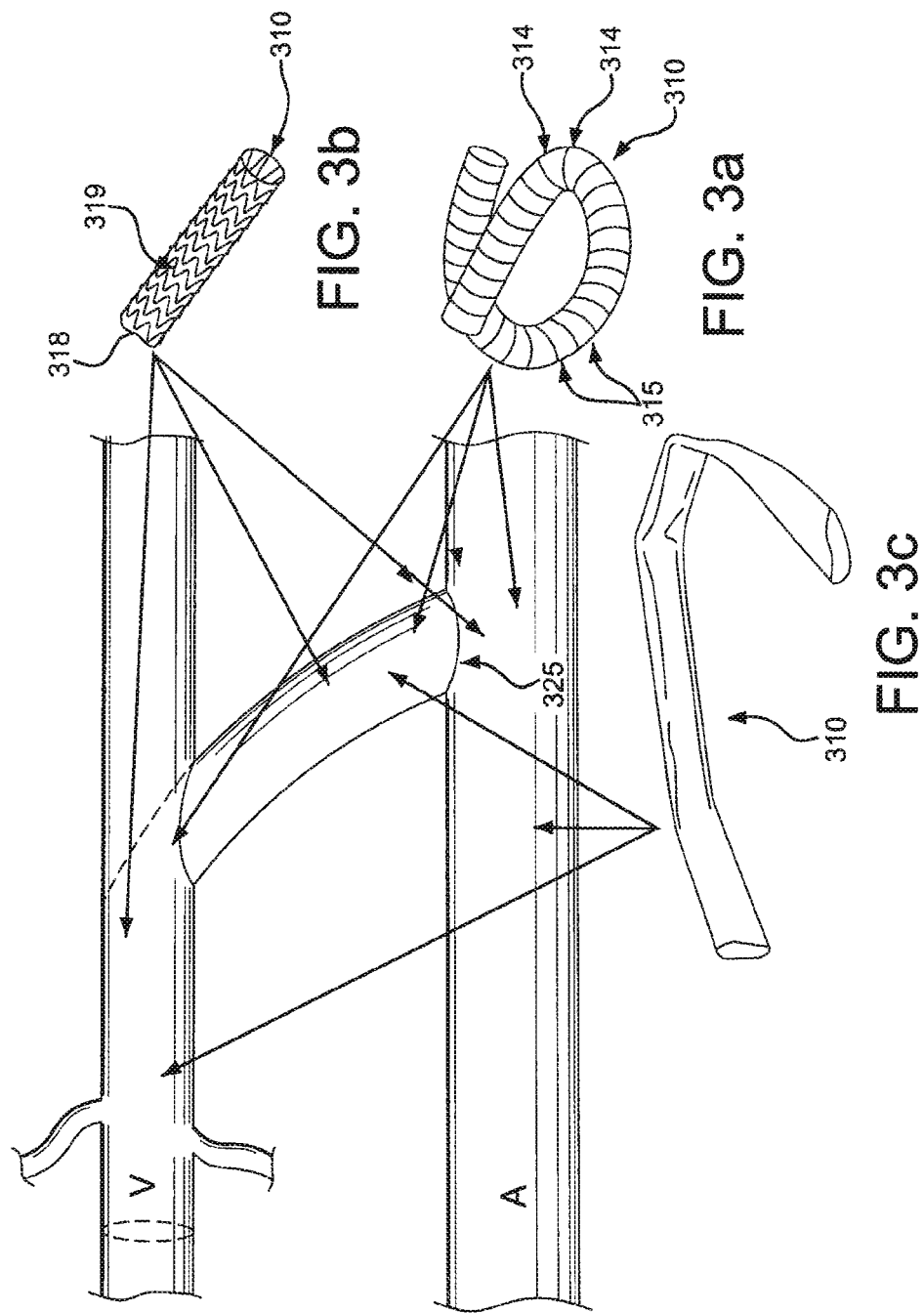

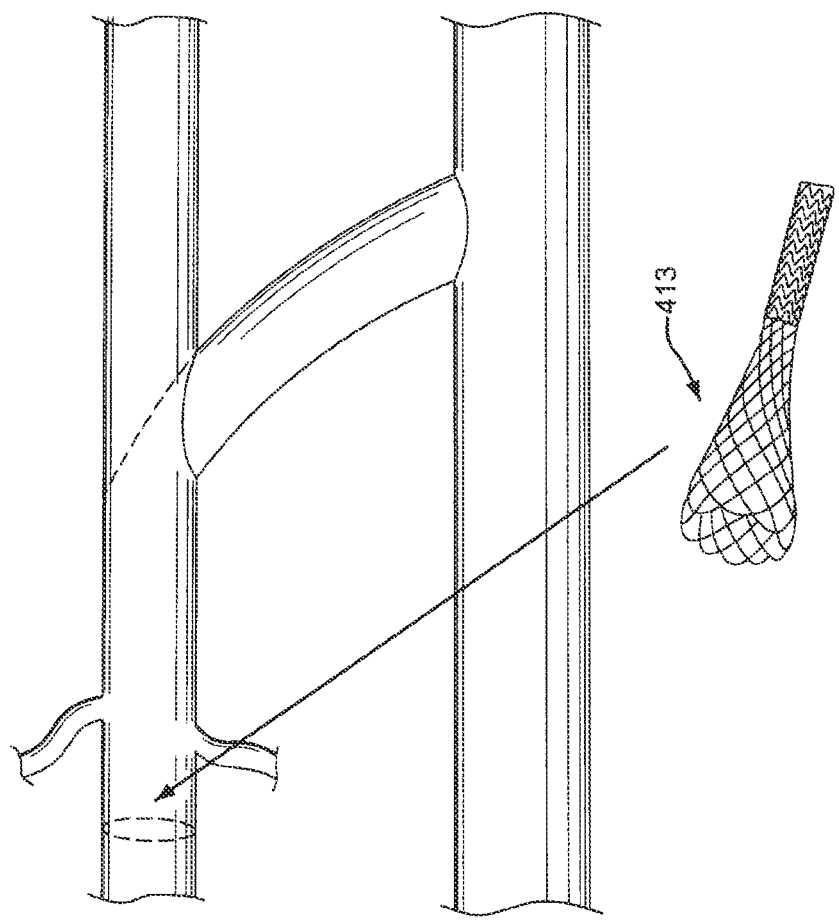

ANASTOMOTIC DEVICES AND METHODS

CROSS REFERENCE RELATED APPLICATIONS

This application is a Continuation of U.S. application Ser. No. 16/291,575, filed Mar. 4, 2019, which is a Continuation of U.S. application Ser. No. 15/267,312, filed Sep. 16, 2016, now U.S. Pat. No. 10,245,371, issued Apr. 2, 2019, which is a Continuation of U.S. application Ser. No. 13/229,540, filed Sep. 9, 2011, now U.S. Pat. No. 9,463,269, issued Oct. 11, 2016, which claims priority to and the benefit of Provisional Application Ser. No. 61/381,655, filed Sep. 10, 2010, all of which are incorporated by reference herein in their entireties.

BACKGROUND OF THE INVENTION

Field of the Invention

The invention relates to anastomotic and blood access devices and methods, more specifically to vascular access fistulas and side-branch devices.

Discussion of the Related Art

In the United States alone, approximately 400,000 people have end-stage renal disease requiring chronic hemodialysis. Hemodialysis replaces kidney function by removing toxins from the blood that are normally removed by healthy kidneys. In order to remove toxins effectively, blood must be passed at a high blood flow rate through a hemodialysis machine. This high blood flow is best achieved by the creation of a permanent vascular access site that includes an arteriovenous (AV) anastomosis in which a vein is attached to an artery to form a high-flow shunt or fistula, commonly referred to as an AV fistula. AV fistulas are widely preferred for use in connection with hemodialysis vascular access based on their superior patency, low complication rates, lower cost to the healthcare system, and decreased risk of patient mortality.

In creating an AV fistula, typically, a vein is directly attached to an artery, and then six to eight weeks from the time of attachment is usually required for the fistula to sufficiently mature, i.e. to provide adequate blood flow, to be cannulated for dialysis, etc. Fistula maturation requires a compliant and responsive vasculature capable of dilating in response to the increased velocity of blood flowing into the newly created low-resistance circuit. Failure to mature of new fistulas remains a major obstacle to increasing the proportion of dialysis patients with fistulas.

In addition, waiting for a fistula to mature exposes those patients in need of more immediate dialysis to increased risk, because a less-desirable temporary access device may be employed. Typically, this temporary access device is a catheter, to be inserted for hemodialysis access until the fistula has matured. The use of a temporary catheter access exposes the patient to additional risk of bleeding and infection, as well as discomfort, and is associated with a 91% higher mortality rate compared to fistulas. In trying to increase the prevalence of fistulas in the U.S., a proportional rise in catheter use has been documented.

Moreover, some people are less than ideal candidates for a fistula. For example, if the vascular system is greatly compromised, a fistula may not be attempted because the implantation may require an invasive surgical procedure that causes trauma to vessel walls and thus, is too risky for those with a weakened vasculature. In addition, AV fistula may not be feasible in all patients due to anatomical considerations.

Accordingly, there is a need for AV fistulas exhibiting the ability to improve the maturation rates of AV fistulas, reduce the instances of AV fistula failure, and minimize the extent of vessel trauma during implantation and thereafter.

SUMMARY OF THE INVENTION

According to one aspect of the invention, a vascular access fistula device has a generally continuous conduit to allow blood flow between an artery and a vein having inner walls after a deployment of the device in a body. The fistula device has an arterial segment that extends into the artery after deployment. The fistula device has a venous segment that extends into the vein after deployment. The fistula device further has a body that extends longitudinally between the arterial segment and the venous segment. The fistula device includes a first flange that extends outwardly from the arterial segment. The first flange mechanically engages an arterial wall upon deployment of the fistula device to secure the fistula device to the artery. The fistula device also includes a compliant support formed on the venous segment that expands outwardly toward the inner walls of the vein. The compliant support is flexible and generally compliant to minimize radial distension of the vein after deployment of the venous segment in the vein. In an exemplary embodiment, the compliant support may be configured to reduce or block retrograde blood flow.

According to another aspect of the invention, a sidewall port device comprises dual flanges and is coupled to a conduit wherein the dual flanges engage an aperture in a vascular wall. Each flange of the dual flanges extends radially outwardly with respect to the aperture in the vascular wall. The flanges mechanically engage both luminal and abluminal surfaces of the arterial wall for fixedly securing the stent graft to the vascular wall and generally creating an end-to-side sutureless anastomosis.

According to another aspect of the invention, a stent graft comprises a sidewall port device having dual flanges for coupling the stent graft to a surgically made aperture in a vascular wall or another stent device. According to another aspect of the invention, a stent graft includes a single flange for coupling a conduit through an aperture in a vascular wall and/or the wall of another stent device. A single flange extends generally radially outwardly from an end of the stent graft and resides in proximity to the luminal wall of vessel and/or stent device upon deployment. The single flange mechanically engages the luminal wall and may be held in place against the vessel wall by fluid pressure and/or an interference fit. The single flange portion reduces the effect of necrosis of the vessel by reducing the pinch force of the vessel wall.

According to another aspect of the invention, a vascular access fistula device may comprise a conduit to allow blood flow between two vessels, such as an artery and a vein, and a flow frame connected thereto or integral with a conduit configured to allow downstream perfusion in addition to transmural flow. Stated differently, the flow frame, which may be comprised of any structure or material (e.g., whether metallic or polymeric), may be configured to not obstruct flow through the native conduit or vessel. In this regard, the flow frame may comprise a branched conduit, an elbow conduit, a stent, a stent graft, a modified stent graft to have a window cutout or bare stent area, a siphon, a conduit occupying only a portion of the luminal cross-section of a vessel, a whisk, a floating whisk, and the like.

Another aspect of the invention comprises a fistula device having a conduit and two flow frames, such as two whisks, wherein a whisk is projecting from each end of the conduit and is configured to be surgically or percutaneously implanted, and further, may be percutaneously maintained.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

FIGS. 3(a) to 3(e) illustrate perspective views of various exemplary conduits;

FIGS. 4(a) to 4(d) illustrate perspective views of various exemplary compliant supports;

DETAILED DESCRIPTION OF THE ILLUSTRATED EMBODIMENTS

Figure 1A:
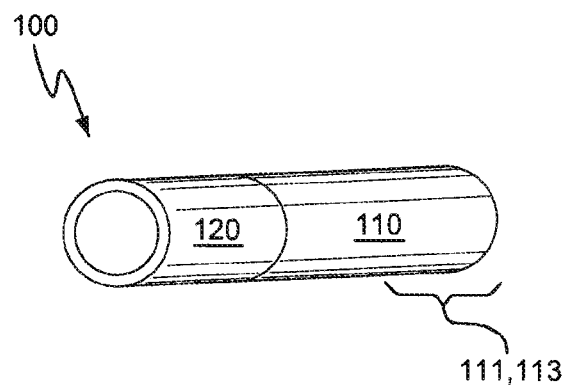
FIG. 1(a) illustrates a perspective view of an exemplary fistula device comprising a sidewall port device.

Persons skilled in the art will readily appreciate that various aspects of the present invention may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various aspects of the present invention, and in that regard, the drawing figures should not be construed as limiting.

Although the present invention may be described in connection with various principles and beliefs, the present invention should not be bound by theory. For example, the present invention is described herein in connection with anastomosis, such as vascular access fistula devices, in the context of hemodialysis in particular. However, the present invention may be applied toward any conduit connecting devices or methods of similar structure and/or function, e.g. in aortic side-branch applications. Furthermore, the present invention may be applied in nonvascular applications and even non-biologic and/or non-medical applications.

Exemplary embodiments of the present invention are directed toward devices and methods for use in anastomosis, and more specifically toward devices and methods for creating new or reinforcing existing side-branch vessels, and/or bridging neighboring vessels together. One aspect of the present invention is directed toward sidewall ports and/or flow frame designs for purposes of creating transmural flow through an aperture in the sidewall of a vessel or stent device. Another aspect of the present invention is directed toward compliant vessel supports to aid in the transition from device to vessel and/or vessel to device, and to promote vessel dilation. In combination, the present invention is directed toward fistula designs modified with sidewall ports, flow frame designs, and/or compliant vessel supports that can be variously selected, interchanged and connected in any combination and configuration to facilitate an anastomotic outcome.

In particular, exemplary embodiments of the present invention are directed toward arteriovenous fistula (AV fistula) designs. Exemplary AV fistula designs may improve fistula circuit maturity rates such that the fistula may be immediately cannulateable and self-sealing and thereby, eliminate the need for a temporary catheter. Exemplary AV fistula designs may reduce the occurrence of stenosis or restenosis while promoting normal vein dilation. Similarly, exemplary AV fistula designs are sutureless and minimize pressure on vessel walls, thereby making the placement and presence of the device less traumatic to a vessel.

Another exemplary embodiment of the present invention is directed toward aortic side-branch devices configured to engage an aortic stent-graft wall.

A fistula device, in accordance with the present invention, is a device configured to connect a first vessel to a second vessel to facilitate flow, e.g., transmural flow. As used in the context of aortic side-branches, a first vessel may comprise an aorta and a second vessel may comprise an aortic side branch. As used in the context of AV fistulas, a first vessel may comprise an artery, and a second vessel may comprise a vein. An AV fistula may direct blood flow from the artery to the vein through a conduit so that the blood pressure at the venous end of the fistula may be sufficient for hemodialysis.

The above examples serve as illustrations of exemplary configurations and these exemplary configurations are used throughout to explain the present invention. However, the present invention contemplates any vessel-to-vessel configuration, vasculature or otherwise, including but not limited to artery-to-vein, vein-to-artery, main branch-to-side branch, and side branch-to-main branch. As such, arterial and venous references are used as a means of explanation and should not be used to limit the scope of the present invention.

A fistula device, in accordance with the present invention, may be implanted surgically or percutaneously, e.g., endovascularly or otherwise. In addition, a fistula device, in accordance with the present invention, may be endovascularly maintained. For a percutaneously implantable embodiment, a fistula device may comprise a compressed configuration and an expanded configuration. Moreover, the fistula device may be self-expandable.

A fistula device, in accordance with the present invention, may comprise any number of the elements selected from the following—sidewall ports, flow frame designs, compliant vessel supports, and conduits—which can be variously selected, interchanged and connected in any combination and configuration to facilitate an anastomotic outcome. Furthermore, each of the elements may be configured to radially expand and contract with its host vessel(s) in an effort to more closely match the compliance of the vessel(s).

Now with reference to FIG. 1(a), in accordance with an exemplary embodiment, a fistula device 100 may comprise a sidewall port device 120 coupled to the end portion of and co-luminal with a conduit 110 to create a branched system. Conduit 110 comprises a tubular component configured to transport a fluid. Conduit 110 may be configured to create a new conduit, e.g. a bridging conduit, connecting two vessels and/or provide support to a preexisting vessel proximate a junction. A distal portion 111 of conduit 110 may be modified to aid in the transition from device 100 to a vessel, a vessel to device 100 or may be modified to have a compliant support 113 attached thereto to promote vessel dilation.

A sidewall port device 120 is a device configured to join two conduits at an angle to create or reinforce a junction of a branched vessel system and/or a bridged vessel system. (Both conduit modifications, bridged and branched systems, are referred to herein as a branched system.) As such, sidewall port device 120 creates a substantially annular seal with the sidewall of a vessel so that a fluid, such as blood flowing through a vessel, does not leak from the branched system. For example, sidewall port device 120 may comprise a single-flanged or double-flanged device configured to extend radially with respect to an aperture in a vessel wall.

Figure 1B:
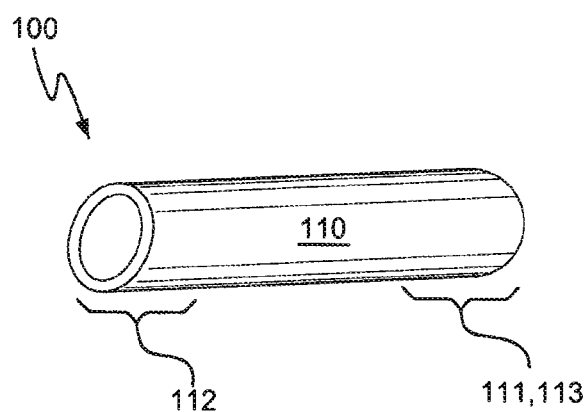
FIG. 1(b) illustrates a perspective view of an exemplary fistula device comprising a flow frame.

In lieu of or in addition to sidewall port 120, with reference to FIG. 1(b), a fistula device 100 may comprise conduit 110 having a proximal portion 112 configured to allow to allow downstream perfusion in addition to transmural flow. For example, conduit 110 may be modified to extend through a first vessel and an aperture in the vessel wall and have a flow frame locatable in the lumen of the first vessel.

Figure 2A:
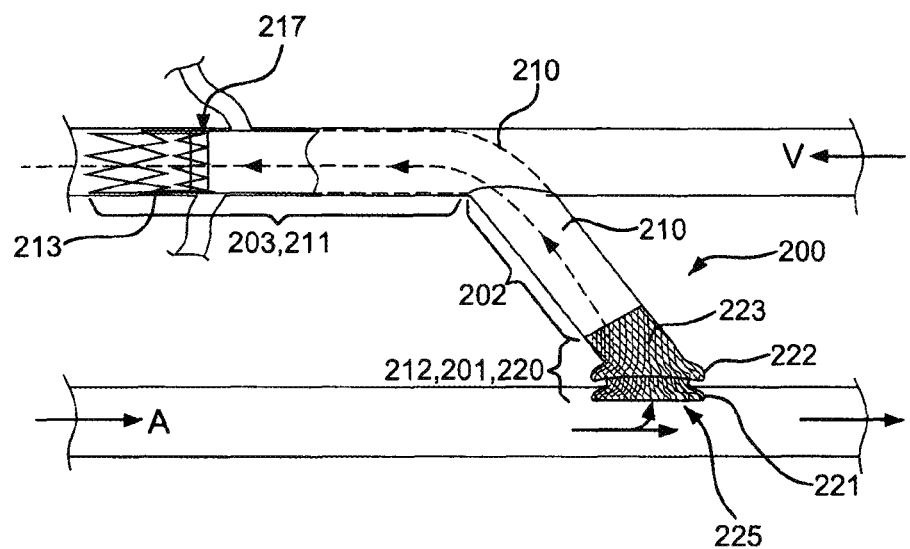
FIG. 2(a) illustrates a longitudinal view an exemplary fistula device shown deployed and coupled to an artery and vein, which are shown cut-away to show portions of the device.

In an exemplary embodiment, with reference to FIG. 2(a), a fistula device 200 comprises an arterial segment 201, body segment 202, and a venous segment 203 having opposite proximal 212 and distal 211 portions. Fistula device 200 includes a generally continuous conduit 210 (the path of which is illustrated by the dotted axis line) that extends between the proximal 212 and distal 211 portions to allow blood flow (as indicated by the arrows) between an artery A and a vein V after a deployment of fistula device 200 in a body of a patient. Upon deployment, arterial segment 201 extends through a fenestration in the artery A. The fenestration may be created surgically or percutaneously, e.g., endovascularly or otherwise. Upon deployment, venous segment 203 extends through a fenestration formed in the vein V. Body 202 extends longitudinally between arterial segment 201 and venous segment 203. Conduit 210 extends through each of the arterial 201, venous 203 and body 202 segments of fistula device 200.

An alternative to fistula device 200 extending through an aperture may comprise one end of a cut vessel repositioned over fistula device 200, such that the cut vessel and fistula device 200 connect, e.g., end to end or overlapping. In this embodiment, the other end would be ligated or otherwise closed off.

Conduit 210 comprises a tubular component configured to transport a fluid. Conduit 210 may comprise a prosthetic or biological material. A tubular component comprises a biocompatible material, whether polymeric or metallic, which can be varied or used in combination to obtain desired support or flexibility properties. A tubular component may be rigid or very flexible and bendable. Similarly, a rigid conduit 210 may comprise a straight or angled configuration as is required by the desired configuration. Conduit 210 when bent, twisted or torqued may be structurally and/or materially configured to do so without kinking. Conduit 210 may also be configured to be length adjustable.

Conduit 210 may also be configured such that the diameter can be customizeable and/or variable such as that disclosed in U.S. Pat. No. 6,336,937 to Vonesh et al., which is incorporated herein by reference. For example, conduit 210 may be deployed at a first diameter, expanded to a second diameter, and enlarged by application of a distensive force, such as through use of a balloon dilatation catheter or via controlled creep processes engineered into conduit 210, to variable third diametrical dimensions to fit the dimensions of the vessel or adjust to changing dimension of the vessel.

For example, with reference to FIG. 3(a), conduit 310 may utilize a bendable or flexible tube design having reduced-diameter sections or indentations 314 that define individual segments 315. Indentations 314 allow the tube to be bent or contorted along a tight curve by elongating on the "outside" of the curve and compressing on the "inside" of the curve. The segments 315 also have an increased radial strength to allow the lumen defined by the tube to remain open when severely bent/distorted during placement and deployment in tortuous anatomy. Adjustability may be achieved by the selective semi-densification of indentation 314 of the tube. Under tension (provided by the implanting clinician) semi-densified indentation 314 will lengthen, thereby allowing the clinical benefit of tailoring the length of fistula device at time of implant.

In another embodiment, with reference to FIG. 3(b), conduit 310 may comprise graft walls 318, such as those made from a thin polymeric material like ePTFE, and/or a stent 319. Stent 319 may comprise any configuration to achieve the preferred amount of bendability and support. For example, stent 319 may comprise a series of wire ring stents or a helical, multi-turn stent which are attached to the graft walls 318 by a film (not shown). The ring or helical turned frame of stent 319 may further comprise undulations (as depicted in FIG. 3(b)) wherein the film only partially covers the wire undulations. This configuration allows conduit 310 to bend within 360 degrees without kinking and improves the conformability of the device to the vessel wall and the ability to traverse through aperture 325.

Another conduit 310, with reference to FIG. 3(c), may comprise a thin, "wispy" tube design such as that disclosed in U.S. Pat. No. 5,800,522, which is incorporated herein by reference. In this embodiment, conduit 310 may circumferentially distend from its initial circumference upon the application of a circumferentially distending force such as applied by an internal pressure, and which exhibits minimal recoil following the removal of the circumferentially distending force. As such, conduit 310 may comprise a second circumference larger than the initial circumference that remains substantially unchanged by further increasing force once it is achieved. A clinician simply trimming the tail of the tube to a desired length may achieve adjustability.

Figure 3D:
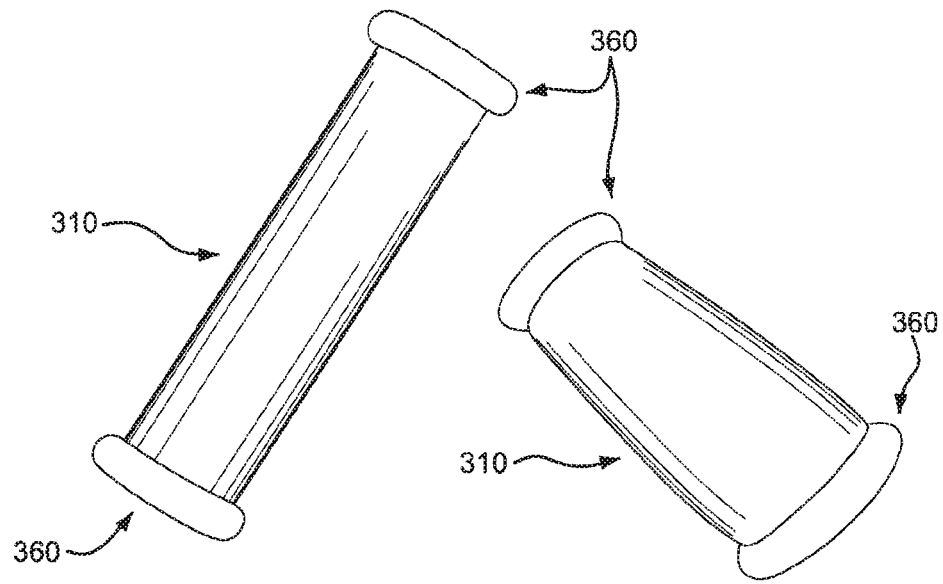
Figure 3E:
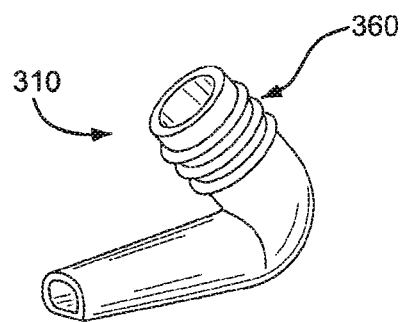
Figure 4A:
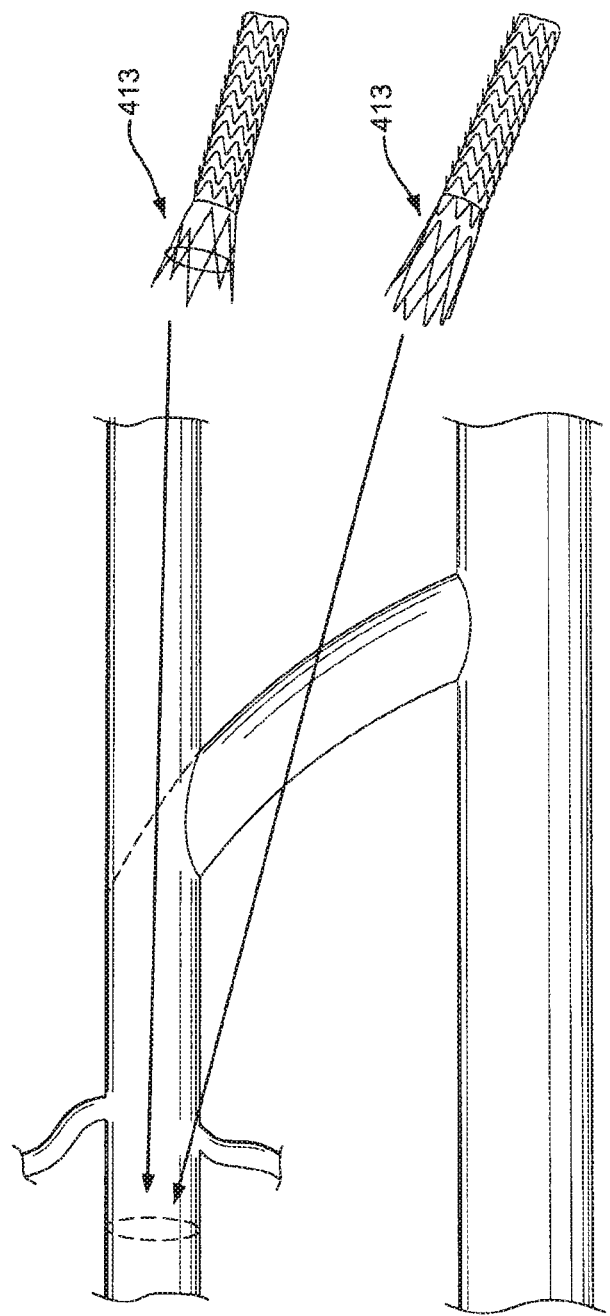
Figure 4B:
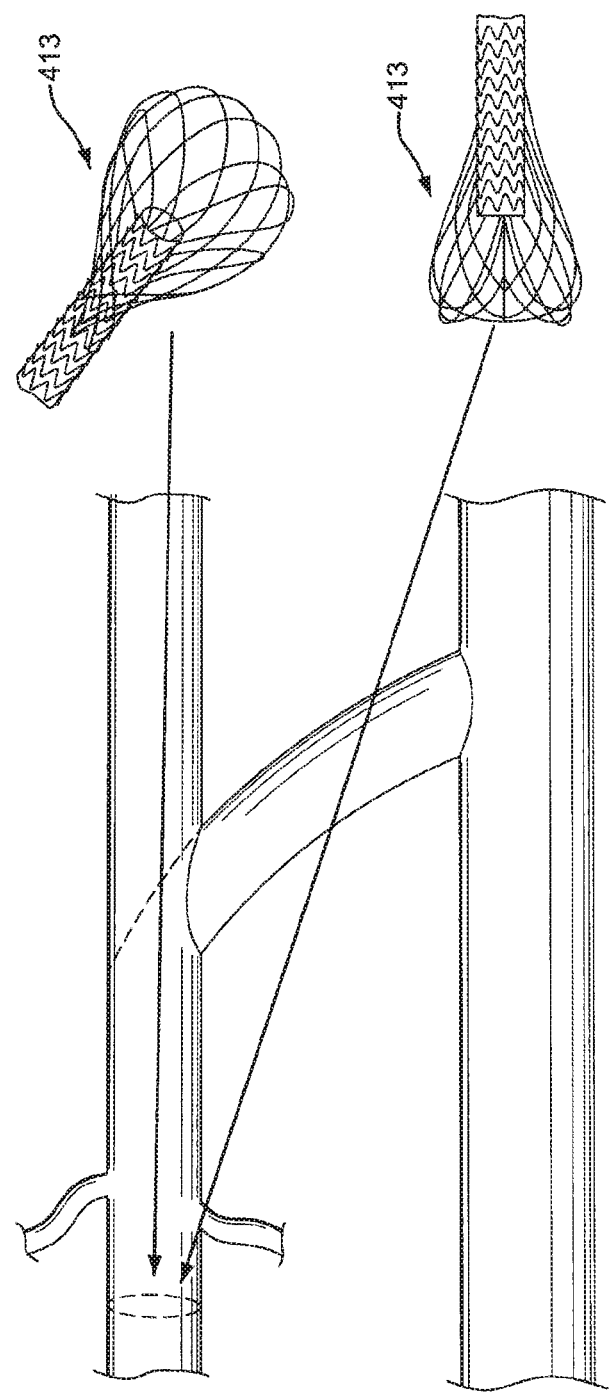
Figure 4D:
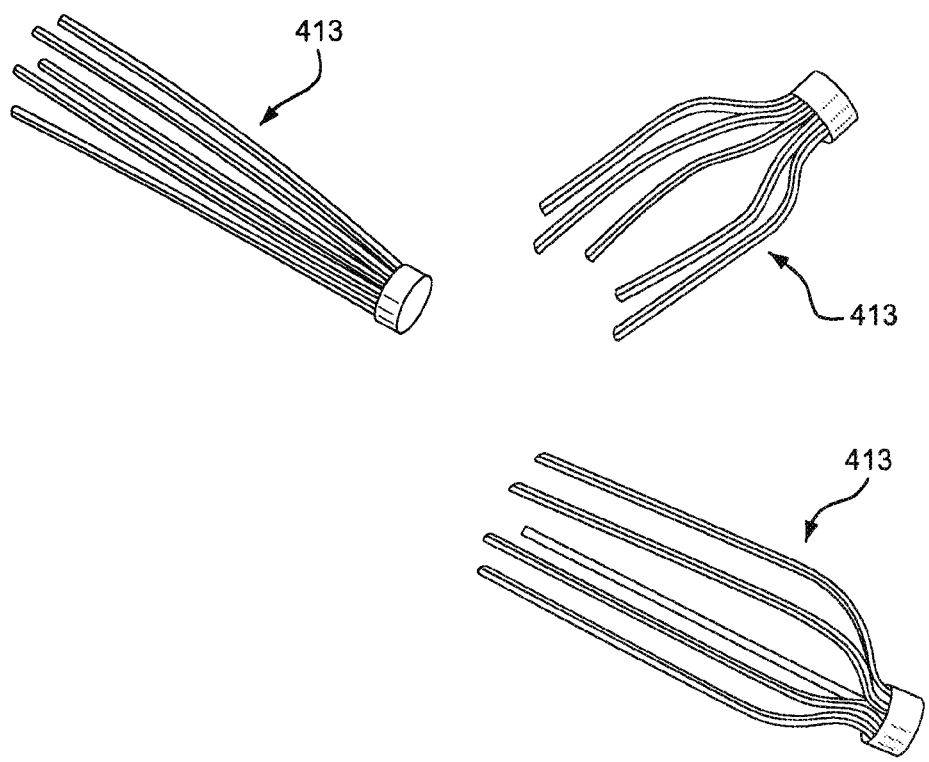

Alternatively, with reference to FIGS. 3(d) and 3(e), conduit 310 may comprise a tubular member that (i) terminates at a junction with a neighboring element and/or (ii) connects end to end with a vessel. In this embodiment, a tubular member may be more rigid and less bendable than the conduit embodiments previously described because conduit 310 is not required to conform to and/or extend through vessels A or V. Conduit 310 may be straight or bent at a preferred angle or curvature suitable for the desired configuration. In an exemplary embodiment, conduit 310 comprises a polymeric material such as ePTFE, and optionally, may comprise, biodegradable material, such as a polyglycolide-co-primethylene carbonate (PGA:TMC) or other similar.

With reference to FIGS. 3(d) and 3(e), conduit 310 may optionally comprise a suture retention ring 360 at a proximal and/or distal end. Suture retention ring 360 may comprise a densified area or an area otherwise reinforced so that an end of a vessel or an aperture in a vessel wall may fit about conduit 310 and be connected thereto in any suitable manner, e.g., by clamping, tying, or suturing the vessel to conduit 310.

Referring back to FIG. 2(a), conduit 210 may comprise a compliant support 213. Compliant support 213 is configured to radially expand and contract with its host vessel in an effort to more closely match the compliance of the vessel. For example, compliant support 213 may be formed within venous segment 203 and expand outwardly (e.g., in a flared configuration) from distal portion 211 of fistula device 200 toward inner walls of the vein V. Compliant support 213 may also be formed within arterial segment 201 or any other area where compliancy is desired or beneficial. Compliant support 213 comprises any flexible structure that once deployed is generally compliant to minimize radial distension of a vessel. In the instance of a percutaneously deployable fistula device 200, compliant support 213 may comprise a compressed configuration and an expanded configuration, and may further have a self-expanding (elastic) or plastic configuration.

Compliant support 213 may have a generally tapered, bell or frusto-conical shape in an uncompressed state. (Exemplary embodiments of compliant support 413 are illustrated in FIGS. 4(a) to 4(d).) For example, compliant support 213 comprises a tapered, bell or frusto-conical frame. The frame of compliant support 213 comprises any biocompatible material, such as Nitinol, that can make a compliant and flexible frame. The frame of compliant support 213 may be formed of metallic or polymeric filament or cut from tubing or both. A filament in turn, may be formed into a closed ended braided design, a criss-cross or over-lapping design, an undulating series of rings or helix, or any other design, which creates a compliant support 213.

Compliant support 213 may be integral with or fixedly secured to fistula device 200 by any suitable mechanism. For example, annular band 217 may secure compliant support 213 to fistula device 200. Annular band 217 may be formed from a flexible film, such as ePTFE. In one embodiment, compliant support 213 is spaced apart from distal portion 212 and coupled thereto solely by the annular band 217. Alternatively or in addition, compliant support 213 may be fixedly secured, for example by welding or suturing to fistula device 200 that forms a part of the venous segment 203.

While not required, compliant support 213 may comprise a flexible film lining, such as ePTFE. In an exemplary embodiment, the flexible film lining may be configured to reduce or block retrograde blood flow. Further, a film lining may enhance or improve cellular in-growth or biocompatibility.

Compliant support 213 may be any configuration that exerts slight, but constant pressure on the vein V. This constant pressure will cause vascular remodeling to occur over time, resulting in eventual dilation of the vein. This dilation may have an upper limit set by compliant support 213. Once remodeling has ceased, compliant support 213 will allow diametrical fluctuation as determined by blood pressure. It is known that changes between systole and diastole, use of medication, and physical exertion all affect blood pressure. Compliant support 213 is configured to radially expand and contract with its host vessel in an effort to more closely match the compliance of the vessel and thereby reduce late outflow stenosis. It should be appreciated that this feature of fistula device 200 could be applied to other regions of mammalian anatomy also with enhanced benefit. Other venous applications are possible, as well as increased efficacy of arterial, esophageal and intestinal devices can be realized.

Figure 2B:
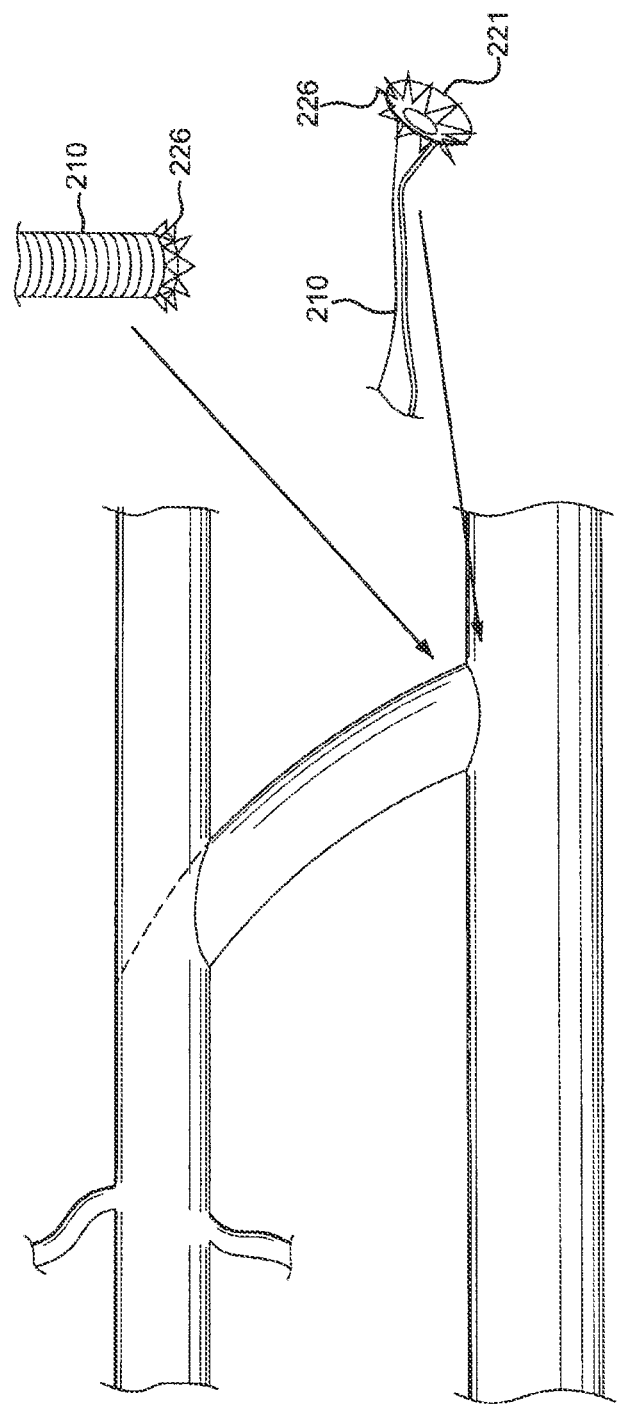
FIG. 2(b) illustrates a side view of an exemplary sidewall port device connected to an exemplary conduit in an uncompressed state.

In an exemplary embodiment, fistula device 200 comprises sidewall port device 220 in the arterial segment 201 coupled to or integral with conduit 210. For example, sidewall port device 220 may comprise a first flange 221, which extends generally radially and generally defines an aperture 225. Upon deployment of fistula device 200, first flange 221 engages an arterial wall to secure fistula device 200 to the artery A. The outer peripheral dimension of flange 221 may range from being only slightly up to substantially larger than aperture 225. In an exemplary embodiment, with reference to FIG. 2(b), first flange 221 may be configured so arterial pressure may press flange 221 against the arterial wall in order to engage the wall. In addition, first flange 221 may also comprise at least one anchor 226, e.g. a hook or the like, to engage the arterial wall. It should be noted that while not required, sidewall port device 220 may further optionally comprise a second flange 222, as also shown in FIG. 2(a).

Figure 2C:
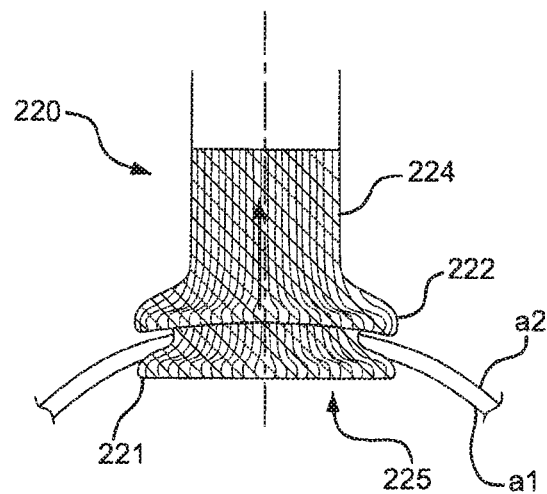
FIG. 2(c) illustrates a side view of a double-flanged end of an exemplary sidewall port device, as viewed in a plane generally orthogonal to the direction of blood flow through the artery.
Figure 2D:
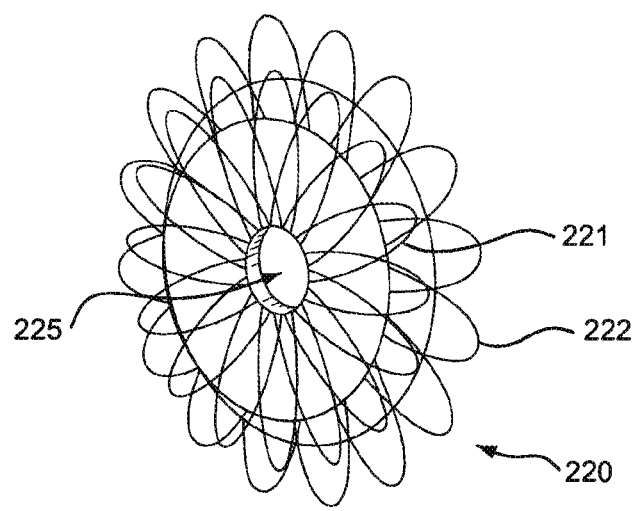
FIG. 2(d) illustrates a perspective view of a double-flanged end of an exemplary sidewall port device.

By way of further example, and with reference to FIG. 2(c) and FIG. 2(d), sidewall port device 220 may comprise a first flange 221 and second flange 222, both which extend generally radially and generally define an aperture 225. The second flange 222 is axially spaced apart from the first flange 221 to receive a portion of a vessel wall there-between upon deployment, such that the first 221 and second 222 flanges are configured to mechanically engage opposite luminal and abluminal surfaces "a1" and "a2" of the vessel wall to secure the sidewall port device 220 and/or a fistula device to the vessel wall.

Flange 221, 222, whether a single or dual configuration, may comprise a lattice 223 (FIG. 2(a)) that is self-expanding or self-setting. For example, lattice 223 may radially and outwardly bias the flanges 221, 222 toward an outer peripheral dimension that is larger than that of aperture 225. When a tension force is applied, flanges 221, 222 elongate to a reduced profile, but when the tension force is removed, built-in bias of lattice 223 facilities flanges regaining their neutral, outer peripheral dimension. For example, lattice 223 may comprise a generally diamond-shaped, petal-like pattern, or any other flexible configuration that can be elongated to reduce its profile and retract back to its neutral, flanged configuration upon relaxation of a tension force. Such reduced profile facilitates a percutaneous placement.

Lattice 223 may be formed from either a single filament or a plurality of filaments. The filaments may comprise a Nitinol, Elgiloy or other suitable biocompatible metals or polymers. The cross-section of the filaments may be round, square, rectangular, oval, polygonal, or other geometric shape. Lattice 223 may be covered or lined in with a flexible polymeric film, such as an expanded polytetrafluorethylene (ePTFE) film. In FIGS. 2(a) through 2(d), both multiple and single filament lattice structures are depicted, but the desired sutureless anastomosis may be achieved with a formed laser-cut tube as well.

Although a self-expanding lattice is preferred (due to implant site proximity to the skin surface and risk of accidental or inadvertent external compression), flange 221, 222 may comprise any collared or rimmed structure that can be fixedly secured to a vessel wall about aperture 225— whether comprised of filament(s), molded feature(s), or otherwise—such as a plastically deformable flange structure as illustrated in FIG. 3(*d*).

In an exemplary embodiment, with reference to FIG. 2(*c*), sidewall port device 220 may comprise first flange 221 and/or second flange 222 formed from a tube 224 comprising lattice 223 inverted onto itself to form an inner tube disposed coaxially within an outer tube. Flanges 221, 222 may be formed along the outer tube. The inner and outer tubes transition at an outer peripheral edge of the first flange. In an exemplary embodiment, tube may further extend from sidewall port device 220 to function as a stent graft, or alternatively a stent graft may be coupled to the sidewall port device 220. However, sidewall port device 220 need not be configured from a tube. Sidewall port 220 comprises any structure having a first flange 221, which extends generally radially and generally defines an aperture 225 and is configured to engage an arterial wall.

It should be readily appreciated that the sidewall port device, e.g., the anchored single flange and dual flanges, and the flow frame described below can be utilized for anchoring and sealing other endoluminal devices, such as stent grafts, in other areas of the vascular system and other bodily conduits, such as aortic side branches, coronary bypass grafts, artificial gastrointestinal stomas and the like. A stent graft according to an alternative embodiment includes dual flanges for coupling the stent graft through a clinically made aperture in a vascular wall or wall of another prosthesis. Each flange of the dual flanges extends radially outwardly with respect to the aperture. Each flange mechanically engages generally opposite sides of the wall surrounding an aperture for fixedly securing the stent graft to the wall. In another embodiment, a stent graft includes a single flange for coupling the stent graft through an aperture in a wall. The single flange extends generally radially outwardly from an end of the graft and resides in proximity to the luminal wall of the artery upon deployment. The single flange mechanically engages the luminal wall and is held in place against the wall by vessel pressure and/or interference fit. The single flange portion reduces the effect of necrosis of the vessel by reducing the pinch force of the vessel wall.

Figure 5A:
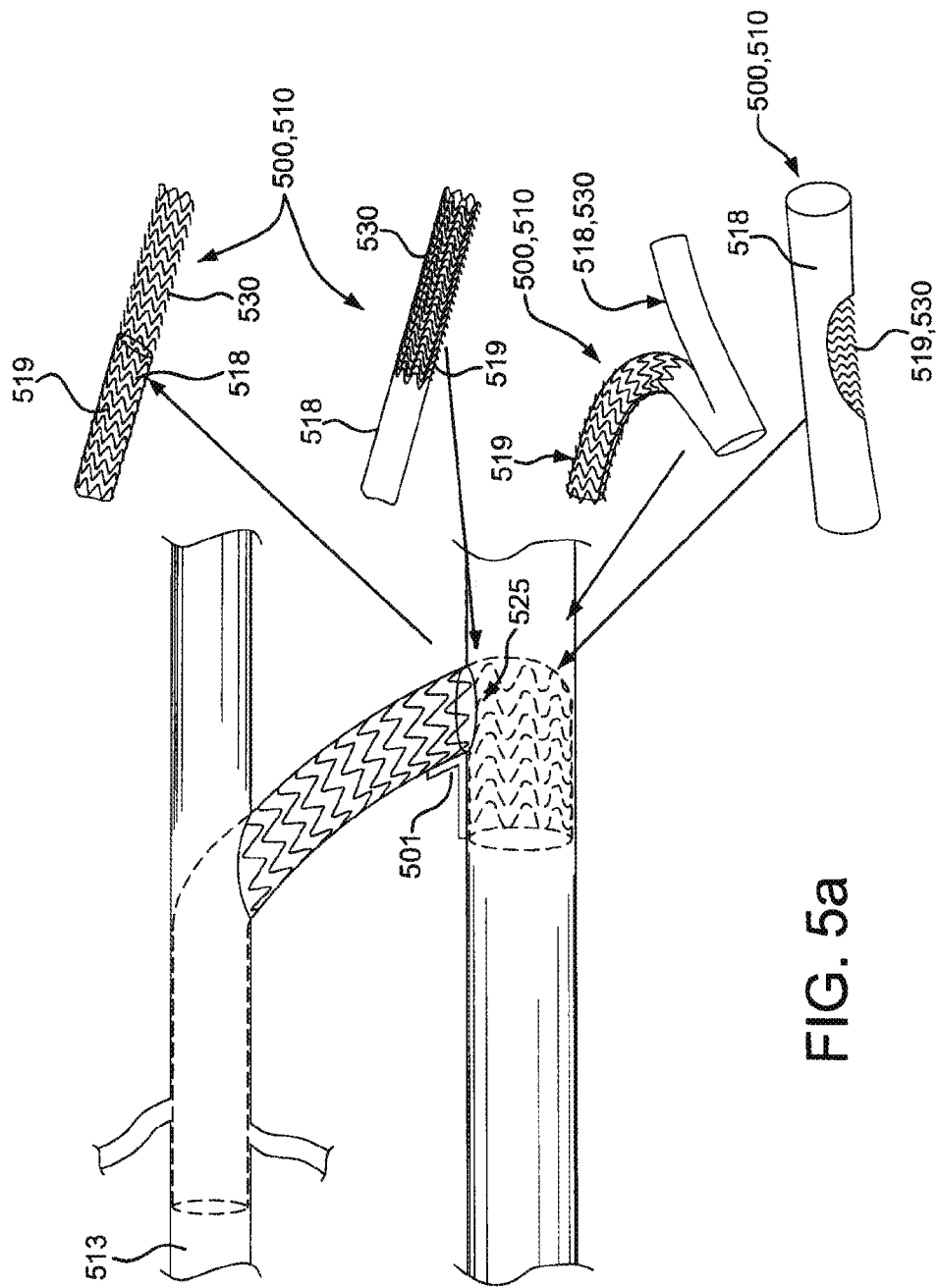
FIG. 5(a) illustrates perspective views of exemplary flow frames comprising conduits.
Figure 5B:
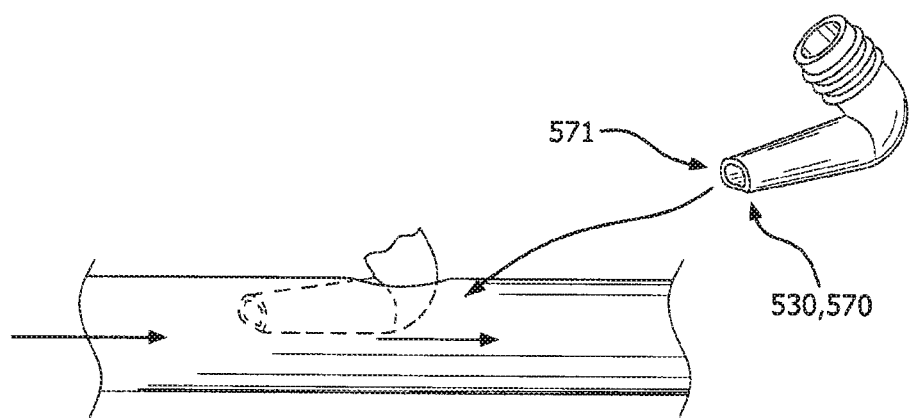
FIG. 5(b) illustrates a perspective view of an exemplary flow frame comprising a siphon conduit.

Now with reference to FIGS. 5(*a*) to 5(*b*), in an exemplary embodiment, fistula 500 comprises a flexible conduit 510, as described above, and a flow frame 530 in arterial segment 501. Fistula 500 may further comprise a compliant support 513, as described above, in venous segment 503.

Flow frame 530 is configured to span at least a portion of the lumen of a vessel proximate the aperture when deployed. Flow frame 530 is usually configured to allow to allow downstream perfusion in addition to transmural flow. Similarly, the present invention contemplates flow frame 530 alternatively configured to block or reduce retrograde blood flow. A portion of flow frame 530 may extend through an aperture in a vasculature wall or prosthetic device.

Flow frame 530 may comprise a compressed configuration and an expanded configuration. Moreover, flow frame 530 may be self-expanding.

For example, flow frame 530 may comprise a portion of conduit 510 comprising stent 519 as describe above with a portion of graft material 518 in the area of an elbow or bend in conduit cut-away, i.e. bare stent 519, to allow downstream perfusion in addition to transmural flow. Graft material 518 may terminate in any fashion to reveal bare stent 519; e.g., graft 518 may terminate at a straight or angled cut to reveal bare stent 519 or be a cutout of any shape and size proximate aperture 525. Other exemplary embodiments of flow frame 530 may comprise a bifurcated branch or a conduit window or opening of any shape locatable at an elbow or bend in conduit 510.

Alternatively, with reference to FIG. 5(*b*), flow frame 530 may comprise a siphon conduit 570 that occupies only a portion of the luminal cross-section of a vessel to allow downstream perfusion in addition to transmural flow. Siphon conduit 570 comprises an inlet 571 sized so as to allow sufficient flow into the diverted segment yet still allow for sufficient downstream perfusion (e.g., in the context of AV fistulas, to minimize the chance of Steal Syndrome).

Figure 6A:
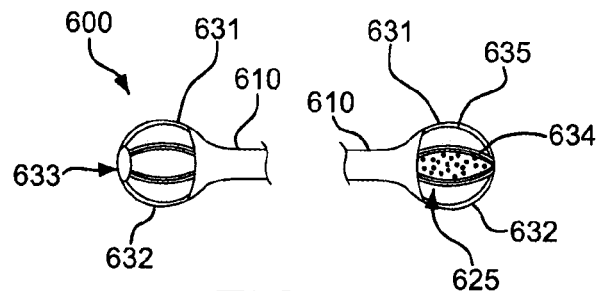
FIG. 6(a) illustrates a side view of an exemplary fistula device comprising two exemplary whisks.

Alternatively, with reference to FIG. 6(*a*), flow frame 630 may comprise whisk 631. Whisk 631 comprises any framework 632 configured to span at least a portion of a lumen proximate an aperture when deployed to allow to allow downstream perfusion in addition to transmural flow. For example, framework 632 may comprise any open structure which when deployed does not block or significantly obstruct flow through the native conduit, e.g. rib(s) or a crisscross structure. Whisk 631 may have a generally curved profile at points of contact to minimize any vessel wall trauma thereabout. Whisk 631 may be composed of any biocompatible material, whether polymeric, metallic or combinations thereof, e.g., ePTFE and/or Nitinol, and may be formed of ribs or interwoven/interconnected bands or cut from tubing or both.

Whisk 631 may comprise a compressed configuration and an expanded configuration. Moreover, whisk 631 may be self-expanding.

Whisk 631 may be configured to allow or re-direct normal blood flow, or reduce or block retrograde blood flow. For example, framework 632 may be partially covered with film 634 and at least partially spanning a lumen cross-section to reduce or block flow. Similarly, whisk 631 may be configured to minimize fluid turbulence, or alternatively to increase fluid turbulence. For example, ribs may comprise a bladed profile that when deployed are positioned in a manner to reduce turbulence.

Whisk 631 may be configured to seal a vessel wall puncture site. For example, whisk 631 may comprise a cap 633 on distal end that when deployed presses against vessel wall opposite aperture 625. A puncture on vessel wall generally opposite aperture 625 would then be sealed by cap. Cap 633 may be further imbibed with a therapeutic agent, such as a localized clotting agent or antibiotic, to further promote sealing and/or improve rate of healing.

Whisk 631 may be integral with or fixedly secured to conduit 610, as described above, by any suitable mechanism. For example, an annular band, as described above, may secure whisk 631 to conduit 610. Annular band is formed from a flexible film or tape, such as ePTFE. Alternatively or in addition, whisk 631 may be fixedly secured, for example by welding or suturing to conduit 610.

Whisk 631 may exert slight, but constant pressure on a vessel. This constant pressure will cause vascular remodeling to occur over time, resulting in eventual dilation of the vessel. This dilation will have an upper limit set by whisk 631. Once remodeling has ceased, whisk 631 may allow diametrical fluctuation as determined by blood pressure. It is known that changes between systole and diastole, use of medication and physical exertion all effect blood pressure. Whisk 631 may be configured to radially expand and contract with its host vessel in an effort to more closely match the compliance of the host vessel and thereby reduce late outflow stenosis.

In an exemplary embodiment, fistula device 600 may comprise conduit 610, a first whisk 631 and a second whisk 635, wherein first whisk 631 is projecting from one end of conduit 610 and the second whisk 635 is projecting from the other end. At least one whisk 631, 635 may comprise cap 633 to seal a puncture site created to percutaneously deploy fistula device 600. Fistula device 600 may be self-expandable.

Figure 6B:
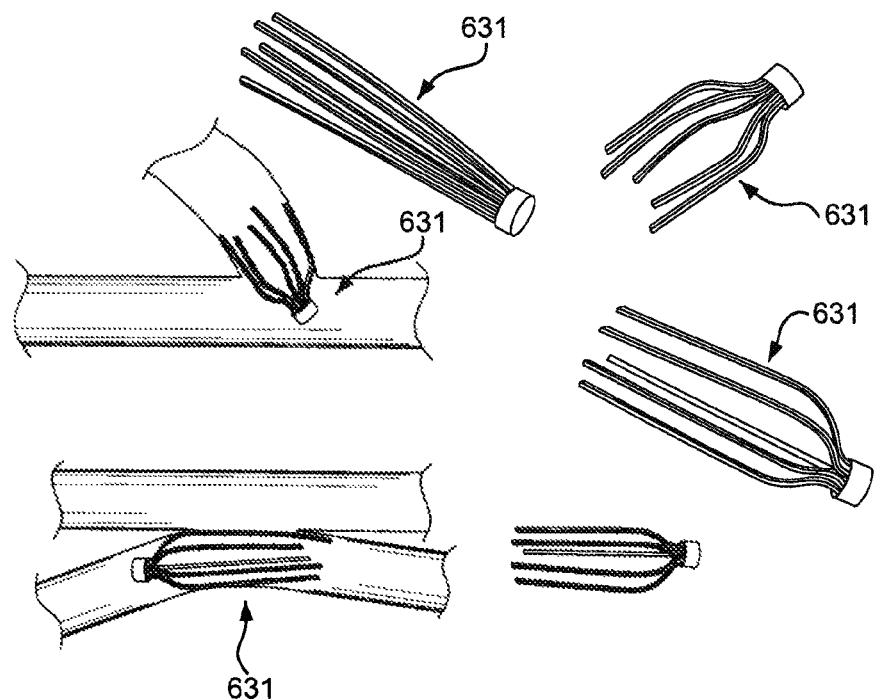
FIG. 6(b) illustrates exemplary floating whisks and a side view of an exemplary floating whisk positioned in a vessel.

With reference to FIG. 6(b), whisk 631, as described above, may also be configured to function as a "floating" whisk 631 to span a portion of, or the entire cross-section of a lumen or aperture. Floating whisk 631 can be positioned anywhere within the lumen of a vessel, fistula device, or prosthetic device, through an aperture or otherwise, for purposes of providing structural support, i.e., holding an aperture or vascular walls open to prevent collapse. Floating whisk 631 may be surgically or endovascularly removable if desired.

The present invention also contemplates methods for implanting surgically or percutaneously a fistula device as described herein, as well as method of performing maintenance endovascularly on a previously implanted fistula device. In exemplary embodiments, the present invention provides for a mature fistula which may be characterized as (i) having at least a 4 mm, more preferably at least a 6 mm diameter, (ii) being less than 8 mm, more preferably less than 6 mm from the skin surface, and/or (iii) facilitating 400 mL/min of blood flow, more preferably 600 mL/min of blood flow.

For example, an exemplary method of delivery may comprise the steps of passing a first catheter through a first vessel wherein the first catheter comprises a side port and ramp to radially direct a flexible piercing device, second catheter; or other elongate member though the sideport. An exemplary piercing device may comprise a continuous lumen there through.

The next step in an exemplary method of delivery may comprise passing the piercing device through the lumen of the first catheter; piercing the sidewall of the first vessel and piercing the sidewall a second vessel with the piercing device; and entering lumen sufficiently to so that a guidewire may enter the lumen of a second vessel as it exits the distal tip of the piercing device. In an exemplary embodiment, the next step may comprise passing a fistula device as described herein, which may be loaded onto a catheter over the guidewire into a desired position for deployment. For example, with regard to an AV fistula, the desired portion may comprise a proximal portion within an arterial segment and a distal portion within a venous segment.

Figure 7A:
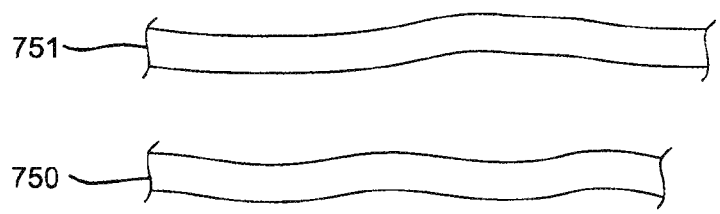
FIGS. 7(a) to 7(c) illustrate an exemplary method of percutaneous delivery of a fistula device.
Figure 7B:
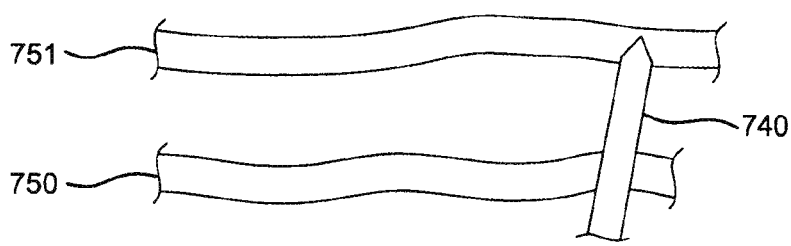
Figure 7C:
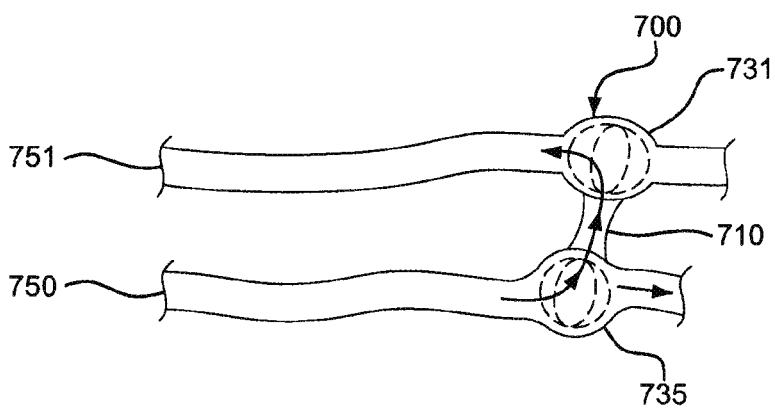

In an exemplary embodiment, with reference to FIGS. 7(a) to 7(c), a method of delivery comprises the steps of passing a hollow needle 740 through a first vessel 750 wherein within the lumen of hollow needle 740, a compressed fistula device 700 comprising conduit 710, first whisk 731 and second whisk 735 as described above resides; entering the lumen of a second vessel 751 with hollow needle 740; deploying first whisk 731 in lumen of second vessel 751; retracting the hollow needle 740 from fistula device 700; and thereby deploying second whisk 735 in first vessel 750. First vessel 750 and second vessel 751 may comprise an artery or a vein.

In an exemplary embodiment, a method of maintenance comprises the steps of endovascularly deploying a balloon or other endovascular tool to the site where a fistula device (as described herein) has been previously implanted for purposes of inspection, repair, or maintenance All components described herein may be imbibed or coated with a therapeutic agent; e.g., heparin or any other antithrombotic agents.

As stated previously, it should be readily appreciated that the embodiments described herein are not an exhaustive recount of all possible embodiments. The components described herein, namely sidewall ports, conduits, flow frames (e.g., modified conduits or whisks), and compliant supports, can be variously selected, interchanged and connected in any combination and configuration to facilitate an anastomotic outcome.

It should be noted that various implantation schemes are envisioned. This device may be surgically implanted or endoluminally deployed in place. Both surgical and endoluminal versions may contain radiopaque markers to assist in 1) initial implantation and 2) subsequent interrogation "maintenance" procedures. The device may come pre-packaged and radially constrained within a delivery system to facilitate accurate and quick placement. This delivery system may be configured long enough for remote access to a vessel, such as from the brachial artery, or very short to be used by a vascular surgeon. The delivery devices and systems will also be configured with imaging enhancements to assist in locating and guiding these devices during use. Enhancements may include echogenic and or radiopaque markers.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method of re-directing fluid flow from a first vessel to a second vessel in a body of a patient, the method comprising:
   forming a fistula between the first vessel and the second vessel;
   introducing a first portion of a fistula device in the first vessel, an intermediate portion of the fistula device in the fistula, and a second portion of the fistula device in the second vessel, the fistula device having a wall defined by a frame and a cover coupled to the frame, the fistula device terminating at a first end corresponding to the first portion and a second end corresponding to the second portion, the first portion having an opening formed through the wall; and
   deploying the fistula device from a first, delivery configuration to a second, expanded configuration, such that the first end of the first portion receives blood flow from the first vessel, permits blood from the first vessel to flow through the opening of the first portion, and the second portion receives blood from the first vessel through the first portion and the intermediate portion and delivers it into the second vessel.

2. The method of claim 1, wherein the first portion defines a bend along a length of the first portion and the opening is positioned at the bend in the first portion, the method further comprising:
   positioning the first end of the fistula device in the first vessel upstream of the bend; and
   positioning the second portion of the fistula device in the second vessel.

3. The method of claim 2, further comprising forming the bend along the length of the first portion.

4. The method of claim 2, wherein the cover defines the opening at the bend of the expandable unbranched frame.

5. The method of claim 4, wherein the frame is an unbranched stent and the opening defined by the cover exposes bare stent.

6. The method of claim 4, wherein the cover terminates at a straight or angled cut.

7. The method of claim 1, wherein the fistula device is introduced into the body percutaneously.

8. The method of claim 1, further comprising perfusing the second vessel with blood flow from the first vessel.

9. A method of deploying a fistula device, comprising:
passing a first catheter through a first vessel;
piercing a first sidewall of the first vessel;
piercing a second sidewall of a second vessel;
passing a first portion including a first end of the fistula device over the first catheter into the second vessel;
deploying the first portion of the fistula device in the second vessel; and
deploying a second portion including a second end of the fistula device in the first vessel so that the fistula device forms a bend between the first end and the second end, the bend being contained within one of the first vessel and the second vessel and allowing downstream flow within the one of the first vessel and the second vessel.

10. The method of claim 9, wherein the first catheter comprises a side port to radially direct an elongate member through the side port.

11. The method of claim 10, wherein the elongate member includes at least one of a piercing member and a second catheter.

12. The method of claim 11, wherein the piercing member is a hollow needle.

13. The method of claim 9, wherein passing the first portion of the fistula device into the second vessel includes passing the first portion of the fistula device over a guidewire.

14. The method of claim 9, wherein the fistula device is preloaded onto the first catheter.

15. A method for directing fluid flow, comprising:
deploying a first portion of an expandable flow frame having a cover in a first vessel;
deploying a second portion of the expandable flow frame in a second vessel in a manner forming a bend between the first portion and the second portion so that the bend corresponds with an opening defined by the cover so that fluid is permitted to flow through the opening and the second portion of the expandable flow frame.

16. The method of claim 15, wherein the first vessel is an artery.

17. The method of claim 15, wherein the second vessel is a vein.

18. The method of claim 15, wherein the opening is positioned opposite of the first portion of the expandable flow frame within the first vessel.

19. The method of claim 15, wherein the opening has edges forming straight lines.

20. The method of claim 15, wherein the cover comprises ePTFE.

* * * * *